United States Patent [19]
Tolman et al.

[11] 3,991,206
[45] Nov. 9, 1976

[54] ALLEVIATION OF EYE INFLAMMATION BY TOPICAL APPLICATION OF p-BIPHENYLACETIC ACID

[75] Inventors: Edward Laurie Tolman, Suffern; Adolph Edward Sloboda, New City, both of N.Y.

[73] Assignee: American Cyanamid Company, Stamford, Conn.

[22] Filed: Jan. 15, 1976

[21] Appl. No.: 649,375

[52] U.S. Cl. .............................................. 424/317
[51] Int. Cl.² ........................................ A61K 31/19
[58] Field of Search .................................... 424/317

[56] References Cited
UNITED STATES PATENTS
3,784,704    1/1974    Cohen et al. ..................... 424/317

FOREIGN PATENTS OR APPLICATIONS
7,166M    2/1970    France

*Primary Examiner*—Stanley J. Friedman
*Attorney, Agent, or Firm*—Neal O. Willmann

[57] ABSTRACT

A method for the treatment of ocular inflammation by the topical application of p-biphenylacetic acid in a pharmaceutically acceptable carrier.

5 Claims, No Drawings

ALLEVIATION OF EYE INFLAMMATION BY TOPICAL APPLICATION OF P-BIPHENYLACETIC ACID

DESCRIPTION OF THE PRIOR ART

The compound p-biphenylacetic acid is known and its preparation described in the literature, F. Blicke, et al., J.A.C.S., 65 1725 (1943). U.S. Pat. No. 3,784,704 also discloses the preparation of p-biphenylacetic acid and its use in producing long lasting amelioration of pain in warm-blooded animals. French Pat. No. 7,166M (Feb. 23, 1970), reports that p-biphenylacetic acid possesses anti-inflammatory, antipyretic and analgesic activity.

Substituted p-biphenylacetic acids are described in Irish Pat. No. 56/65, Belgian Pat. No. 664,187 (11-19-65), South African Pat. No. 65/4206 (3-10-66) and French Pat. No. 2401M (4-13-64). These patents describe a variety of uses for the substituted p-biphenylacetic acids. Esters of biphenylacetic acid are described in the above-mentioned F. Blicke, et al. reference as antispasmodics. Other references such as British Pat. No. 034,534 (1-14-71) and T. Y. Shen, Chim. Ther., 2 (3), 459 (1959), describe a number of substituted biphenylacetic acids as anti-inflammatory agents. To the best of our knowledge, no art is known which is concerned with the use of p-biphenylacetic acid to treat inflammation of the eye.

SUMMARY OF THE INVENTION

This invention discloses a method for alleviating ocular inflammation in warm-blooded animals by administering topically to the eyes of said animals an anti-inflammatory amount of p-biphenylacetic acid in a pharmaceutically acceptable carrier.

DESCRIPTION OF THE PREFERRED EMBODIMENT

The utility of p-biphenylacetic acid as a topical ocular anti-inflammatory agent has been established in the following tests.

The effects of p-biphenylacetic acid on arachidonic acid induced increased intraocular pressure (IOP) and aqueous humor protein levels in rabbits, both symptoms of acute ocular inflammation, were studied in the following manner. Adult, female New Zealand white rabbits, weighing 2–2.5 kg, were held immobile in specially designed metal restraining devices and IOP levels were monitored on a tonometer, calibrated by the manufacturer for this species. Protein concentrations were estimated by the standard Lowry, et al. method [Lowry, O. H., Rosebrough, N. J., Farr, E. L. and Randall, R. J., Protein Measurement with the Folin Phenol Reagent, J. Biol. Chem., 193, 265–275 (1951)], in aqueous humor samples taken by paracentesis as described below.

Specifically, rabbits were allowed a 30 minute acclimation period before experimentation was begun. Only one eye of each rabbit was used per test and one drop of 0.5% proparacaine hydrochloride, a topical anesthetic, was applied just prior to each IOP measurement as paracentesis. Baseline IOP values were established for each animal in each experiment by averaging the last three recordings made at 15 minute intervals for at least 1 hour prior to application of the test compound or its vehicle.

p-Biphenylacetic acid in a light mineral oil suspension or mineral oil alone was applied topically over the entire corneal surface 10 minutes prior to arachidonic acid application and subsequent IOP recordings were made at 15 minute intervals beginning 15 minutes after arachidonic acid application. The maximum change (expressed also as an increase) from baseline IOP in response to the arachidonic acid challenge was quantitated by subtracting the average baseline level for each animal from the highest IOP level recorded 15 to 45 minutes after challenge. Aqueous humor samples were taken 30 minutes after challenge. Paracentesis was performed by withdrawing 0.15 to 0.20 ml of fluid from the anterior chamber of the eye via a 30 gauge needle into a 0.5 ml syringe.

In these experiments p-biphenylacetic acid was applied topically as 2 drops (approximately 0.05 ml) of a light mineral oil suspension in the concentrations indicated. Arachidonic acid was dissolved in mineral oil to give a final concentration of 2% and 2 drops of this solution were applied over the entire corneal area.

The results of applying various levels of p-biphenylacetic acid 10 minutes prior to an arachidonic acid challenge are shown in Table I.

TABLE I

| TREATMENT | NUMBER OF ANIMALS | AVERAGE INCREASE IN IOP (mm Hg) + 1 SEM* |
| --- | --- | --- |
| 2% Arachidonic Acid + Vehicle | 20 | 10.2 ± 1.1 |
| p-Biphenylacetic Acid 5% | 4 | 0.82 ± 0.41** |
| p-Biphenylacetic Acid 2.5% | 7 | 2.4 ± 0.66** |
| p-Biphenylacetic Acid 1% | 11 | 3.5 ± 0.54** |
| p-Biphenylacetic Acid 0.5% | 8 | 4.9 ± 1.3** |
| p-Biphenylacetic Acid 0.1% | 8 | 5.6 ± 0.70** |

*SEM = Standard error of the mean
**Differs significantly from arachidonic acid alone by $P \leq .005$ A more detailed presentation of the results obtained in a similar experiment using the arachidonic acid challenge is shown in Table II.

TABLE II

Time courses of the effects of various challenges with or without p-biphenylacetic acid pretreatment on rabbit intraocular pressure in mm of mercury. Each figure represents an average ±1 standard error of the mean.

| CHALLENGE | PRE-TREATMENT | NUMBER OF ANIMALS | PRE-CHALLENGE TIME (MINUTES) | | | | | POST-CHALLENGE TIME (MINUTES) | | | | MAXIMUM CHANGE (15–45 MINUTES AFTER CHALLENGE) |
| --- | --- | --- | --- | --- | --- | --- | --- | --- | --- | --- | --- | --- |
| | | | 70 | 55 | 40 | 25 | 10 | 15 | 30 | 45 | 75 | |
| None (Mineral Oil) | None | 6 | 22 ±1 | 21 ±.8 | 20 ±.6 | 23 ±.5 | 20 ±.8 | 23 ±.8 | 21 ±.8 | 23 ±.8 | 22 ±.5 | +2.9±.9* |

TABLE II-continued

Time courses of the effects of various challenges with or without p-biphenylacetic acid pretreatment on rabbit intraocular pressure in mm of mercury. Each figure represents an average ±1 standard error of the mean.

| CHALLENGE | PRE-TREATMENT | NUMBER OF ANIMALS | PRE-CHALLENGE TIME (MINUTES) | | | | | POST-CHALLENGE TIME (MINUTES) | | | | MAXIMUM CHANGE (15–45 MINUTES AFTER CHALLENGE) |
|---|---|---|---|---|---|---|---|---|---|---|---|---|
| | | | 70 | 55 | 40 | 25 | 10 | 15 | 30 | 45 | 75 | |
| Arachidonic Acid (2%) | None | 16 | 21 ±.9 | 20 ±.6 | 19 ±.6 | 19 ±.6 | 19 ±.5 | 27 ±1 | 27 ±1 | 24 ±1 | 18 ±.8 | +9.5±1 |
| Arachidonic Acid (2%) | p-Biphenylacetic Acid (5%) | 11 | 21 ±1 | 20 ±1 | 18 ±.8 | 18 ±1 | 19 ±1 | 21 ±1 | 21 ±.8 | 20 ±1 | 18 ±.8 | +3.4±1* |

*Significantly different from challenge (arachidonic acid alone) by $P < .005$.

The effects of the topical application of p-biphenylacetic acid on aqueous humor composition following arachidonic acid challenge are shown in Table III, together with aqueous humor prostaglandin levels which were estimated using a commercially available radioimmunoassay kit.

TABLE III

Effect of p-Biphenylacetic acid on arachidonic acid-induced changes in aqueous humor protein and prostaglandin levels.

| | | 30 MINUTES POST-CHALLENGE | |
|---|---|---|---|
| CHALLENGE | PRETREATMENT | PROTEIN (mg/ml) | PROSTAGLANDIN (ng PROSTAGLANDIN B EQUIV./ml) |
| Mineral Oil | None | .63 ±.09(6)* | Not Determined |
| Arachidonic Acid | None | 2.87 ±.61(11) | .70 ±.10(4) |
| Arachidonic Acid | p-Biphenylacetic Acid (5%) | .50**±.02(11) | .30***±.03(4) |

*Mean of the number of observations given in parenthesis ±1 standard error of the mean
**$P < .001$ versus non-pretreated arachidonic acid group; $P > .10$ versus mineral oil challenge group
***$P < .01$ versus non-pretreated arachadonic acid group A less specific method of producing ocular inflammation in rabbits is by akali burn, using the topical application of 0.02 ml of 2N sodium hydroxide. The inhibitory effects of pretreatment with p-biphenylacetic acid on increased IOP due to base challenge are shown in Table IV.

hours later. Prior to paracentesis, eyes were examined for iridial redness and aqueous humor samples analyzed for protein concentrations. Drug treatment, or the topical application of p-biphenylacetic acid (0.5% suspension in 0.5% carboxymethyl cellulose) or 0.1% dexamethasone suspension, commenced 4 hours prior

TABLE IV

| CHALLENGE | PRE-TREATMENT | NUMBER OF ANIMALS | PRE-CHALLENGE TIME (MINUTES) | | | | | POST-CHALLENGE TIME (MINUTES) | | | | MAXIMUM CHANGE (15–45 MINUTES AFTER CHALLENGE) |
|---|---|---|---|---|---|---|---|---|---|---|---|---|
| | | | 70 | 55 | 40 | 25 | 10 | 30 | 60 | 90 | 135 | |
| 0.02 ml 2N NaOH | None | 3 | 22*** ±2 | 21 ±.7 | 22 ±1 | 21 ±.7 | 20 ±.7 | 42* ±5 | 35 ±6 | 28 ±8 | 24 ±4 | +20.7±5 |
| 0.02 ml 2N NaOH | p-Biphenylacetic Acid (5%) | 3 | 19 ±2 | 21 ±.7 | 21 ±2 | 21 ±.7 | 21 ±1 | 26 ±1 | 19 ±3 | 20 ±1 | 19 ±5 | +4.6±1** |

*IOP of one rabbit exceeded upper limit (50 mmHg) of recorder
**Significantly different from challenge (NaOH) above by $P < .05$
***mmHg Paracentesis was used as a third method of producing a very mild ocular inflammatory response. The effects of p-biphenylacetic acid pretreatment on IOP levels following paracentesis are shown in Table V.

to intravitreal albumin challenge and continued every hour on the hour until 4 hours after challenge on day 9 and then again every hour on the hour for 5 hours prior to paracentesis. There were a total of 14 applications.

TABLE V

| CHALLENGE | PRETREATMENT | NUMBER OF ANIMALS | PRE-CHALLENGE TIME (MINUTES) | | | | POST-CHALLENGE TIME (MINUTES) | | | | | | MAXIMUM CHANGE (15–45 MINUTES AFTER CHALLENGE) |
|---|---|---|---|---|---|---|---|---|---|---|---|---|---|
| | | | 55 | 40 | 25 | 10 | 15 | 30 | 45 | 60 | 75 | 90 | |
| Paracentesis | None | 4 | 22** ±1 | 20 ±.7 | 22 ±.1 | 21 ±.5 | 25 ±2 | 22 ±2 | 18 ±1 | 16 ±1 | 18 ±2 | 18 ±2 | +4.0±1 |
| Paracentesis | p-Biphenylacetic Acid (5%) | 4 | 24 ±1 | 22 ±1 | 21 ±2 | 20 ±2 | 8 ±3 | 6 ±3 | 8 ±3 | 8 ±4 | 10 ±4 | 10 ±4 | −16.1±3* |

*Differs significantly from challenge (paracentesis) above by $P < .01$
**mmHg

An immunogenically induced model of acute anterior uveitis, a common form of ocular inflammation, was established as follows. Rabbits, as described above, received subcutaneous injections of 10 ml each of a sterile 5% bovine serum albumin in 0.9% saline solution on days 1, 3, 5 and 8 of the experiment. On day 9, 0.05 ml of the albumin solution was injected intravitreally into each eye and paracentesis was performed 24

Only left eyes were treated with drug. The results of these experiments are shown in Table VI.

TABLE VI

| CHALLENGE | DRUG TREATMENT | NUMBER OF ANIMALS | REDNESS (+ OR −)* LEFT EYE | RIGHT EYE | AQUEOUS HUMOR PROTEIN CONCENTRATION mg/ml LEFT EYE | RIGHT EYE |
|---|---|---|---|---|---|---|
| Saline Injection | None | 3 | − | − | 3.1±1.2** | 4.3±3.8 |
| 5% Bovine Serum Albumin | None | 7 | + | + | 12.5±2.9 | 10.6±2.8 |
| 5% Bovine Serum Albumin | p-Biphenylacetic Acid 0.5% | 3 | − | − | 1.6±.2 | 5.3±3.5 |
| 5% Bovine Serum Albumin | Dexamethasone*** 0.1% | 4 | − | − | 2.5±.8 | 5.6±4.5 |

*+ = redness present; − = redness absent
**Average of the given number of observations ±1 standard error of the mean
***Maxidex ophthalmic suspension (Alcon)

The compound p-biphenylacetic acid may be prepared for ophthalmic topical application in the form of an ointment, an oil suspension or a solution at concentrations ranging from 0.1 to 5.0% with concentrations of 0.5 to 1.0% being preferred. The following examples describe in detail the formulation of p-biphenylacetic acid into various types of pharmaceutical preparations.

Example 1

Preparation of Ophthalmic Solution

| Ingredient | Amount |
|---|---|
| p-Biphenylacetic acid | 0.5–1.0% |
| Boric acid | 1.5% |
| Benzyl alcohol | 0.9% |
| Water for Injection qs to | 100% |
| Sodium Hydroxide to adjust pH to | 7.5–8.5 |

The boric acid is dissolved in a portion of the water for injection. The p-biphenylacetic acid is added and sufficient 5% sodium hydroxide solution is added to produce a complete solution. The benzyl alcohol is added and the balance of the water for injection. The final solution is sterilized by filtration through a 0.22 millimicron millipore filter and filled into individual ampules.

Example 2

Preparation of Ophthalmic Ointment

| Ingredient | Amount |
|---|---|
| p-Biphenylacetic acid | 0.5–1.0% |
| Mineral oil NF | 15.0% |
| Lanolin USP | 10.0% |
| White Petrolatum USP qs to | 100% |

The white petrolatum and lanolin are heated to 50°–55° C and then mixed in a kettle while maintaining the temperature at 50°–52° C. A portion of the mineral oil is placed in a kettle and the p-biphenylacetic acid is added and mixed until a homogenous dispersion is obtained. This dispersion is added to the petrolatum-lanolin mixture and the balance of the mineral oil is added as a rinse. The ingredients are cooled to 31°–32° C with continuous agitation, sterilized and filled into individual tubes.

Example 3

Preparation of Ophthalmic Oil Suspension

| Ingredient | Amount |
|---|---|
| p-Biphenylacetic acid | 0.5–1.0% |
| Plastibase* | 20% |
| Mineral Oil qs to | 100% |

*Plastibase is a blend of polyethylene in mineral oil and/or white petrolatum sold by E. R. Squibb.

The p-biphenylacetic acid is suspended in one-half the volume of mineral oil and then added to the balance of the mineral oil containing the plastibase. The ingredients are thoroughly mixed, sterilized and filled in individual vials.

We claim:

1. A method for alleviating ocular inflammation in a warm-blooded animal which comprises administering topically to the eye of said animal an anti-inflammatory amount of p-biphenylacetic acid in a pharmaceutically acceptable carrier.

2. A method in accordance with claim 1 wherein the p-biphenylacetic acid is incorporated in an ophthalmic solution.

3. A method in accordance with claim 1 wherein the p-biphenylacetic acid is incorporated in an ophthalmic ointment.

4. A method in accordance with claim 1 wherein the p-biphenylacetic acid is incorporated in an ophthalmic oil suspension.

5. A therapeutic composition for the alleviation of ocular inflammation in a warm-blooded animal comprising an effective amount of p-biphenylacetic acid in a pharmaceutical carrier suitable for ophthalmic administration.

* * * * *